United States Patent
Lucas et al.

(10) Patent No.: US 10,948,472 B2
(45) Date of Patent: Mar. 16, 2021

(54) DISCRETE EMISSIONS DETECTION FOR A SITE

(71) Applicant: Halliburton Energy Services, Inc., Houston, TX (US)

(72) Inventors: Bruce Carl Lucas, Marlow, OK (US); Andrew Silas Clyburn, Noble, OK (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 16/464,173

(22) PCT Filed: Dec. 29, 2016

(86) PCT No.: PCT/US2016/069122
§ 371 (c)(1),
(2) Date: May 24, 2019

(87) PCT Pub. No.: WO2018/125119
PCT Pub. Date: Jul. 5, 2018

(65) Prior Publication Data
US 2020/0103388 A1    Apr. 2, 2020

(51) Int. Cl.
*G01N 33/00* (2006.01)
*E21B 41/00* (2006.01)
*G05B 13/02* (2006.01)

(52) U.S. Cl.
CPC ..... *G01N 33/0075* (2013.01); *E21B 41/0021* (2013.01); *G01N 33/0063* (2013.01); *G05B 13/024* (2013.01)

(58) Field of Classification Search
CPC ............ G01N 33/0075; G01N 33/0063; E21B 41/0021; E21B 43/11; G05B 13/024
See application file for complete search history.

(56) References Cited

U.S. PATENT DOCUMENTS

| 7,508,520 B1 * | 3/2009 | Lines ................. G01N 21/3504 |
| | | 250/338.5 |
| 8,793,114 B2 | 7/2014 | Shafer et al. |
| 9,189,944 B2 | 11/2015 | Johnson, Jr. et al. |

(Continued)

FOREIGN PATENT DOCUMENTS

| WO | 2012/047861 A2 | 4/2012 |
| WO | 2016/094338 A1 | 6/2016 |
| WO | 2017/192154 A1 | 11/2017 |

OTHER PUBLICATIONS

International Search Report and Written Opinion issued in related PCT Application No. PCT/US2016/069122 dated Sep. 7, 2017, 10 pages.

*Primary Examiner* — Charles R Kasenge
(74) *Attorney, Agent, or Firm* — John W. Wustenberg; Baker Botts L.L.P.

(57) ABSTRACT

Undetected emissions may damage devices at a work site and pose a safety hazard to the surrounding environment. A method of control based on predictive emissions detection is disclosed. The method uses sensors coupled to work site equipment to identify devices and regions of a work site that may be affected by adverse conditions. Detection of such emissions may allow the system or operator to shut down or otherwise act on equipment before any harm is done to the device or personnel in the area.

20 Claims, 5 Drawing Sheets

(56) References Cited

U.S. PATENT DOCUMENTS

| | | | | |
|---|---|---|---|---|
| 9,322,735 B1* | 4/2016 | Tan | | F02M 65/006 |
| 9,482,591 B2* | 11/2016 | Rella | | G01M 3/20 |
| 9,500,556 B2* | 11/2016 | Rella | | G01N 21/3504 |
| 9,557,240 B1* | 1/2017 | Tan | | G01M 3/00 |
| 9,599,529 B1* | 3/2017 | Steele | | G01N 33/0075 |
| 9,599,597 B1* | 3/2017 | Steele | | G01W 1/02 |
| 9,618,417 B2* | 4/2017 | Rella | | G01M 3/20 |
| 9,645,039 B1* | 5/2017 | Tan | | G01W 1/00 |
| 9,719,879 B1* | 8/2017 | Tan | | F02M 65/006 |
| 9,739,758 B2* | 8/2017 | Rella | | G01N 33/0009 |
| 9,823,231 B1* | 11/2017 | Steele | | F17D 5/02 |
| 10,113,997 B2* | 10/2018 | Rella | | G01N 33/0009 |
| 10,126,200 B1* | 11/2018 | Steele | | G01M 3/04 |
| 10,161,825 B2* | 12/2018 | Rella | | G01M 3/20 |
| 10,203,311 B2* | 2/2019 | Risk | | G01N 33/0009 |
| 10,240,998 B2* | 3/2019 | Prasad | | G01M 3/202 |
| 10,267,729 B2* | 4/2019 | Jones | | G01N 21/3103 |
| 10,330,555 B1* | 6/2019 | Tan | | F02M 65/006 |
| 10,337,859 B2* | 7/2019 | Kreitinger | | G01M 3/38 |
| 10,337,946 B1* | 7/2019 | Tan | | G06F 16/29 |
| 10,386,258 B1* | 8/2019 | Steele | | G01M 3/04 |
| 10,444,108 B1* | 10/2019 | Steele | | G01W 1/02 |
| 10,466,132 B1* | 11/2019 | Tan | | G06F 15/00 |
| 10,598,562 B2* | 3/2020 | Steele | | G01M 3/04 |
| 2011/0137568 A1* | 6/2011 | Bradley | | G01V 9/007 |
| | | | | 702/11 |
| 2014/0026641 A1* | 1/2014 | Rella | | G01N 21/01 |
| | | | | 73/30.01 |
| 2014/0032129 A1* | 1/2014 | Rella | | G01N 21/3504 |
| | | | | 702/23 |
| 2014/0032160 A1* | 1/2014 | Rella | | G01N 21/3504 |
| | | | | 702/127 |
| 2015/0007638 A1* | 1/2015 | Rella | | G01N 21/01 |
| | | | | 73/40 |
| 2015/0219609 A1 | 8/2015 | Soundarrajan et al. | | |
| 2016/0010445 A1 | 1/2016 | Harrison et al. | | |
| 2016/0146696 A1* | 5/2016 | Steele | | G01C 21/3697 |
| | | | | 702/51 |
| 2016/0161456 A1* | 6/2016 | Risk | | G01P 13/02 |
| | | | | 702/24 |
| 2016/0216172 A1* | 7/2016 | Rella | | G01M 3/38 |
| 2016/0247117 A1 | 8/2016 | Rogers et al. | | |
| 2017/0097274 A1* | 4/2017 | Thorpe | | G06K 9/00201 |
| 2017/0097302 A1* | 4/2017 | Kreitinger | | G06K 9/00201 |
| 2017/0185905 A1* | 6/2017 | Eberbach | | G08B 21/12 |
| 2017/0191898 A1* | 7/2017 | Rella | | G01N 21/01 |
| 2017/0336281 A1* | 11/2017 | Waxman | | G01N 33/0036 |
| 2018/0045596 A1* | 2/2018 | Prasad | | G01M 3/16 |
| 2018/0216932 A1* | 8/2018 | Kreitinger | | G01N 21/53 |
| 2019/0086287 A1* | 3/2019 | Rella | | G01N 21/31 |

* cited by examiner

DISCRETE EMISSIONS DETECTION FOR A SITE

CROSS-REFERENCE TO RELATED APPLICATION

The present application is a U.S. National Stage Application of International Application No. PCT/US2016/069122 filed Dec. 29, 2016, which is incorporated herein by reference in its entirety for all purposes.

TECHNICAL FIELD OF THE INVENTION

The present disclosure relates generally to detecting emissions at a site or location, and more particularly, to a method and system for detecting emissions at identified areas or regions of a site or location and controlling equipment associated with the identified areas or regions.

BACKGROUND

In various operations, certain types of equipment may be exposed to emissions or generate emissions, such as hazardous gases. When exposed to emissions, such equipment may experience or be placed in an abnormal, adverse, or undesirable operation mode that may cause damage to the equipment. For example, an engine may experience a run-away mode or overspeed mode causing damage to the engine. Additionally, such emissions may cause harm to the environment or operators. Traditionally, various detection systems have been used to detect the presence of combustible gases and initiate a response (for example, shutting down equipment, sending alerts, etc.) when concentration levels reach a critical level. However, in the event of sudden changes in a concentration level of one or more emissions, the concentration level may reach critical levels before the detection system can respond. Generally, predefined set points to trigger a specific response are utilized, which result in frequent false alarms or shutdowns reducing the effectiveness of the detection system.

BRIEF DESCRIPTION OF THE DRAWINGS

For a more complete understanding of the present disclosure and its features and advantages, reference is now made to the following description, taken in conjunction with the accompanying drawings, in which.

DETAILED DESCRIPTION

Figure 1:
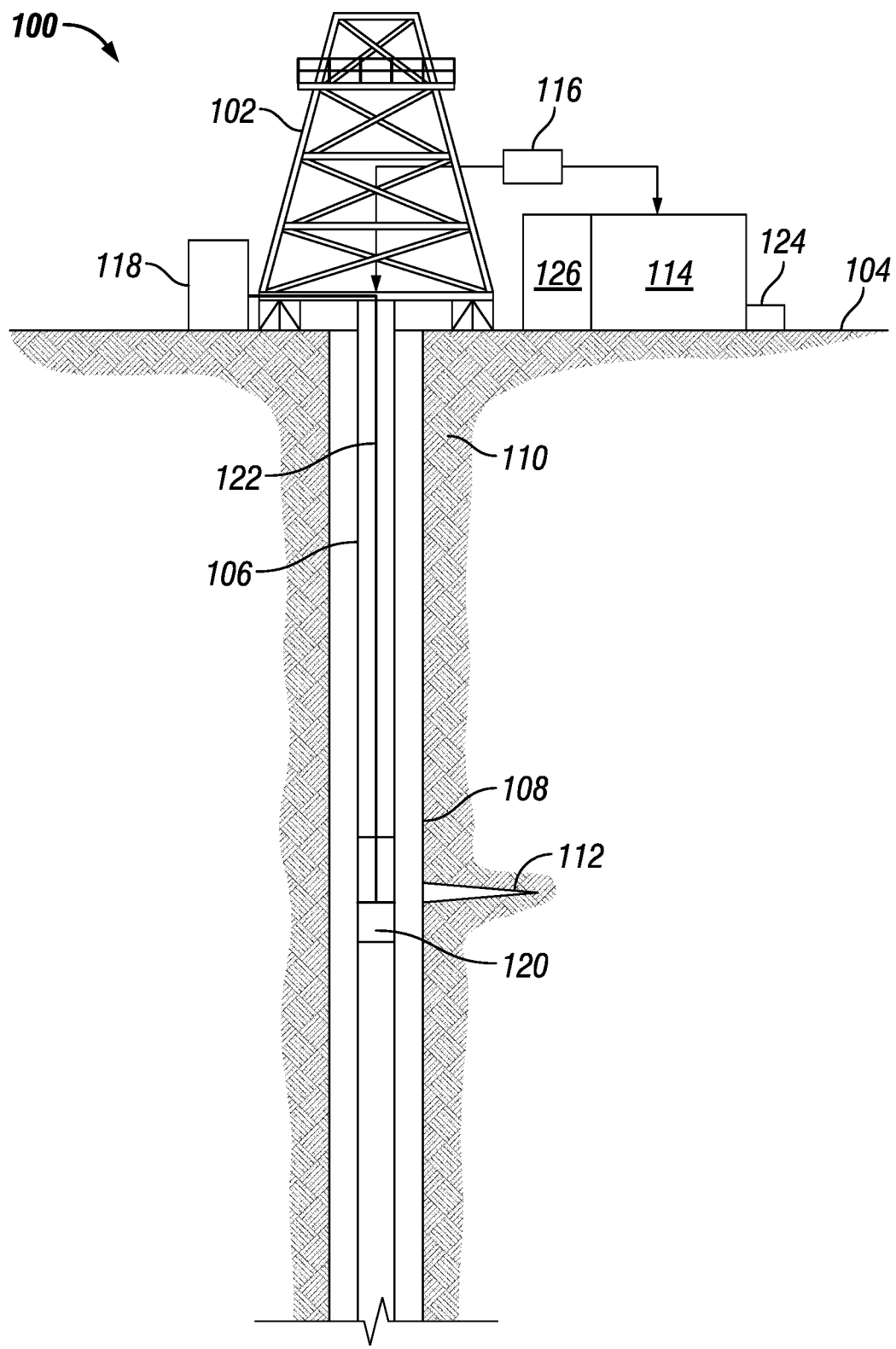
FIG. 1 is a schematic view of a wellbore servicing system, according to one or more aspects of the present disclosure.

Illustrative embodiments of the present disclosure are described in detail herein. In the interest of clarity, not all features of an actual implementation are described in this specification. It will of course be appreciated that in the development of any such actual embodiment, numerous implementation-specific decisions must be made to achieve developers' specific goals, such as compliance with system related and business related constraints, which will vary from one implementation to another. Moreover, it will be appreciated that such a development effort might be complex and time consuming, but would nevertheless be a routine undertaking for those of ordinary skill in the art having the benefit of the present disclosure. Furthermore, in no way should the following examples be read to limit or define the scope of the disclosure.

One or more embodiments of the present disclosure may comprise an information handling system. For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer, a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communication with external devices as well as various input and output (I/O) devices, such as a keyboard, a mouse, and a video display. The information handling system may also include one or more buses operable to transmit communications between the various hardware components. The information handling system may also include one or more interface units capable of transmitting one or more signals to a controller, actuator, or like device.

One or more embodiments, according to the present disclosure, may be directed to systems and methods for controlled shut-off of a combustion engine. A combustion engine may use a combustion mixture (that comprises a type of fuel and an oxidizer (for an oxygen source) for combustion), for example, a diesel reciprocating engine and a turbine engine which may be gas or liquid fueled. Turbine engines, for example, use a spark for ignition on start-up but operate without a spark after a nominal auto-ignition speed has been reached. A combustion engine may be shut-off after start-up by removing or altering the combustion mixture. Control of the shut-off of a combustion engine is important to prevent damage to the combustion engine, such as during a run-away condition, and to prevent potentially unsafe conditions or operation of the combustion engine. For example, abrupt shut-off of a combustion engine may damage components of the combustion engine or cause increased wear and tear of one or more parts or components of the combustion engine. Also, one or more conditions associated with the combustion engine or the location of the combustion engine may occur that affect shut-off of the combustion engine. For example, one or more abnormal or adverse conditions may include, but are not limited to, release of natural gas into the atmosphere, one or more fuel sources mixing with the combustion mixture, and removal or decoupling of a load associated with the combustion engine. In one or more embodiments, concentration levels of one or more emissions are detected and the combustion mixture for the combustion engine is controlled or altered to effectively, efficiently, and safely maintain an operation mode of the combustion engine.

Various aspects of the present disclosure may be implemented in various environments and locations. For example, FIG. 1 is a diagram showing an illustrative well system 100 with a perforating tool system 120, according to aspects of the present disclosure. The well system 100 includes a derrick 102 positioned at a surface 104. The derrick 102 may support components of the well system 100, including a tubing string 106. The tubing string 106 may include segmented pipes that extend below the surface 104 and into a wellbore 108. The wellbore 108 may extend through subterranean formations 110 in the earth adjacent to the wellbore 108. The subterranean formations 110 may include a perforation, an opening or a fracture 112, referred to generally herein as fracture 112. In some aspects, the fracture 112 may be a separation of the subterranean formation 110 forming a fissure or crevice in the subterranean formations 110. In additional aspects, the fracture 112 may be created by a fracturing process in which highly pressured fluid (gas or liquid) is forced into the formations 110 via perforating tool system or assembly 120. A motor or engine 126 may be coupled to a pump 114 to provide a source of power to the pump 114. A pump 114 may be positioned at the surface 104 proximate to the wellbore 108 to pump a fluid into the wellbore. The fluid may be pumped into the wellbore at a rate to expand the fracture 112 or to fill a perforation or fracture 112. The fracture 112 may serve as a path for the production of hydrocarbons from subterranean reservoirs. A pumping device 116 may be included to inject additional fluid into the fracture 112 to further open or extend the fracture 112 in the subterranean formation 110.

The perforating tool system 120 may be coupled via an electrical connection 122 to a control unit 118 at the surface 104. In one or more embodiments, electrical connection 122 may be any material suitable for conveying an electrical signal including but not limited to a wireline, one or more cables (such as a detonator cable), or any other suitable conductive wire or connection. Perforating tool system 120 may be configured according to any one or more aspects of the present disclosure.

In one or more embodiments, control unit 118 may be positioned at or remote from the wellbore environment 100. In one or more embodiments, one or more sensors 124 may be disposed or positioned about the wellbore environment 100. The one or more sensors 124 may detect one or more concentration levels of one or more emissions from wellbore 108, tubing string 106, pumping device 116, pump 114, any other site equipment at wellbore environment 100, or any combination thereof. The one or more sensors 124 may be positioned or disposed on or about pumping device 116, pump 114, any other site equipment at wellbore environment 100, or any combination thereof. The one or more sensors 124 may also be positioned or disposed at any other location at the wellbore environment 100 to detect one or more concentration levels of one or more emissions at, near, or from any site equipment. One or more sensors 124 may be communicatively coupled to the control unit 118. The one or more sensors 124 may transmit information associated with the detected concentration levels to the control unit 118. Control unit 118 may be coupled (directly or indirectly, wired or wirelessly, or any other type of coupling) to pumping device 116, pump 114, or any other site equipment at the wellbore environment 100.

Figure 2:
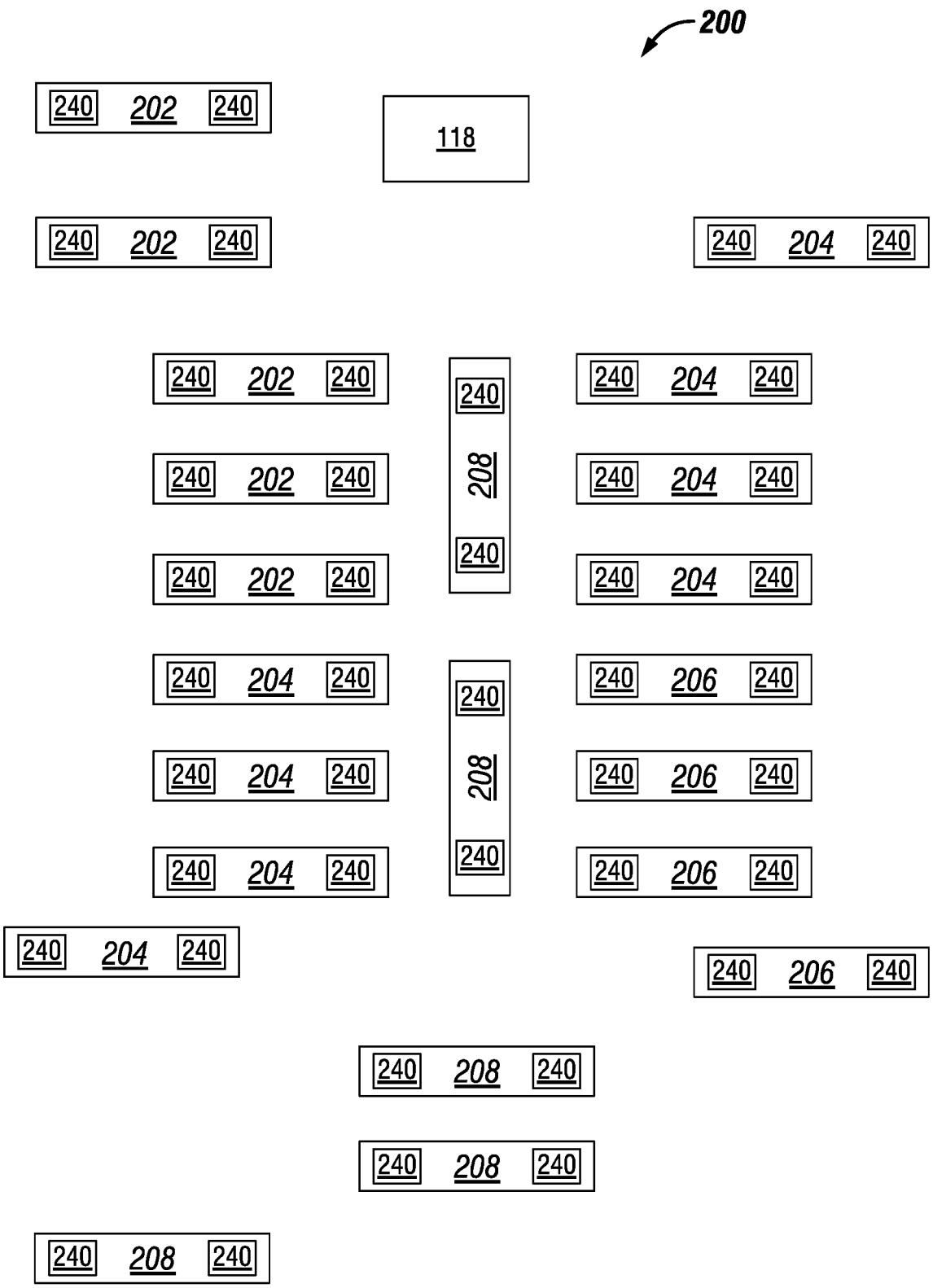
FIG. 2 is a schematic diagram illustrating an example of an emissions detection and equipment control system at a location, according to one or more aspects of the present disclosure.

FIG. 2 is a diagram illustrating an example of an emissions detection and equipment control system 200 at a location, according to the aspects of the present disclosure. The emissions detection and equipment control system 200 may comprise one or more site equipment or devices 202, 204, 206, and 208, one or more sensors 240, and a control unit 118. The one or more devices 202 may comprise any one or more of an engine, a tank, a pump, a generator, or any other type of site equipment. For example, in one or more embodiments, an emissions detection and equipment control system 200 may comprise a single device 202, for example, a single engine. In one or more embodiments, a device 202 may comprise one or more motors or engines, device 204 may comprise one or more pumps, device 206 may comprise one or more tanks or fluid containers, and device 208 may comprise one or more generators. While FIG. 2 illustrates devices 202, 204, 206, and 208 disposed or positioned in a configuration, the present disclosure contemplates that devices 202, 204, 206, and 208 may be disposed or positioned in any configuration and that any configuration may comprise any number or quantity of devices 202, 204, 206, and 208, any other site equipment or devices, or any combination thereof.

Figure 3:
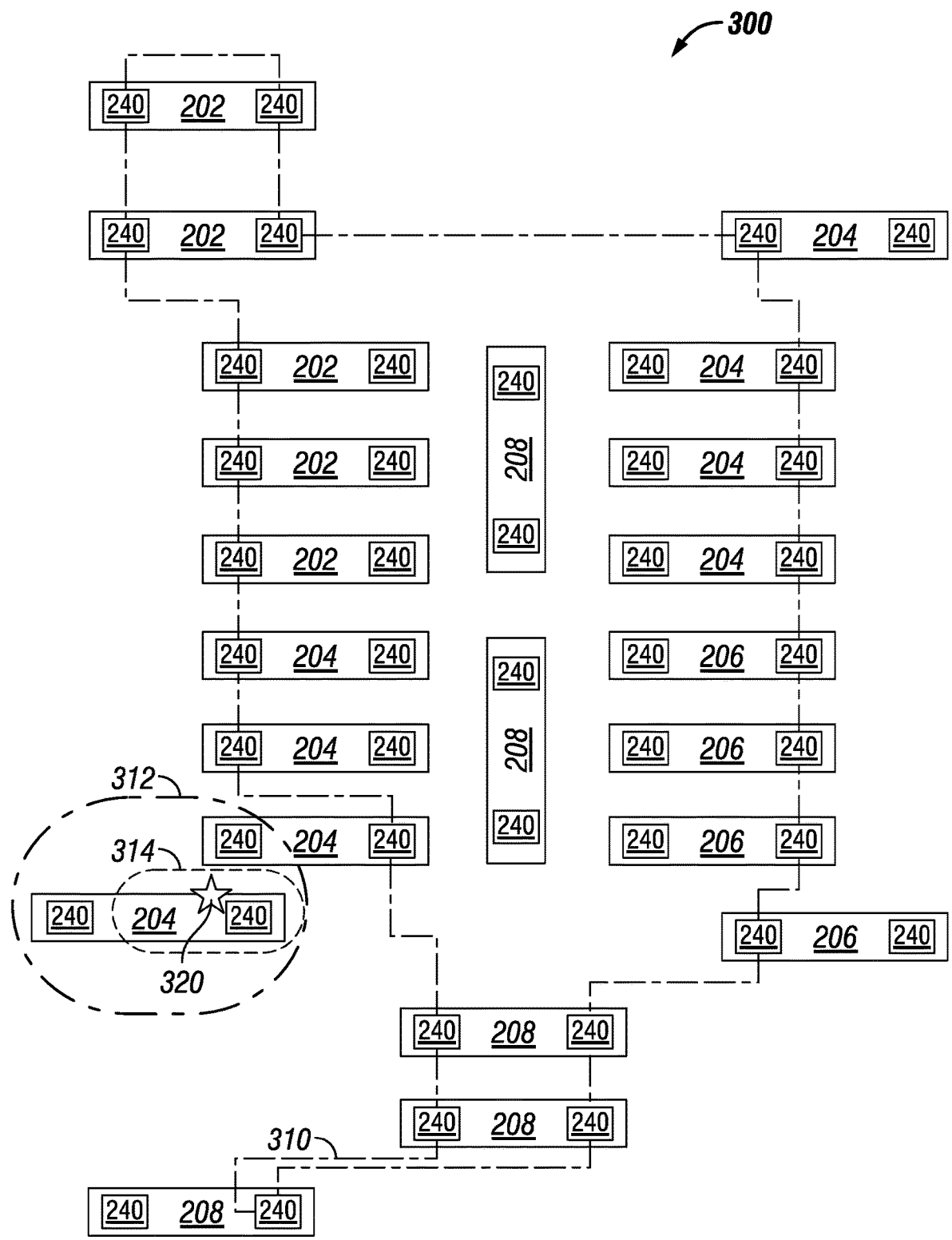
FIG. 3 is a schematic diagram illustrating a mapping of one or more concentration level contours associated with an emissions detection and equipment control system at a location, according to one or more aspects of the present disclosure.

A mapping of the emissions detection and equipment control system 200 may be generated that illustrates a configuration or physical location of the emissions detection and equipment control system 200 and one or more concentration level contours (for example, concentration level contours 310, 312, and 314 illustrated in FIG. 3). In one or more embodiments, a map of all devices 202, 204, 206, and 208 on the location 200 may be generated by one or more user inputs. For example, a user may manually enter the position of each device based on, for example, a site survey. In one or more embodiments, a global positioning system (GPS) technology may be used to generate a mapping of the one or more devices 202, 204, 206, and 208 and any one or more associated or coupled sensors 240. Any one or more of the one or more devices 202, 204, 206, and 208, one or more sensors 240, control unit 118, or any other site equipment may comprise the GPS technology. In one or more embodiments, a map of one or more devices 202, 204, 206, and 208 at or about the location 200 may be generated by one or more other location detection or sensing models, systems, services, or devices, including, but not limited to, network node triangulation systems, global navigation satellite system (GNSS), GPS aided GEO augmented navigation system (GAGAN), and any one or more other satellite navigation systems.

Any one or more devices 202, 204, 206, and 208 may comprise one or more sensors 240 or may have one or more associated sensors 240. In one or more embodiments, a sensor 240 may be attached or coupled directly to any one or more devices 202, 204, 206, and 208. In one or more embodiments, a sensor 240 may be attached or coupled indirectly, for example, through an electrical wire or other connection or wirelessly to any one or more devices 202, 204, 206, and 208. A sensor 240 may detect one or more conditions, for example, a concentration of one or more types of emissions associated with any one or more devices 202, 204, 206, or 208 or any other site equipment. One or more types of emissions may comprise, but are not limited to, a gas, a fluid, a vapor, a noise, a light, a particulate or matter, or any other type of emission or any combination thereof. In one or more embodiments, an emission or type of emission may be classified as hazardous or non-hazardous. For example, one or more hazardous emissions may comprise any one or more of carbon dioxide and hydrogen sulfide, and a non-hazardous emission may comprise oxygen. In one or more embodiments, classification of an emission as hazardous or non-hazardous may be based, at least in part, on one or more of a detected concentration level of the emission or a threshold. For example, an emission comprising oxygen may be classified as non-hazardous when an associated concentration level is below a predetermined threshold and as hazardous when the associated concentration level is above a predetermined threshold.

A sensor 240 may transmit information regarding a detected emission or a concentration of an emission to an information handling system, for example, control unit 118. The information handling system may display (or transmit to any other display) a mapping, table, chart, graphical representation, or any other depiction that illustrates a concentration level of an emission or a type of emission detected by any one or more sensors 240. For example, a concentration level of an emission or a type of emission may be displayed as a discrete value at a time or as a plot of multiple values over a period of time. A type of emission or a concentration level of an emission may be associated with any one or more devices 202, 204, 206, and 208, any grouping of devices 202, 204, 206, and 208, an area, region, or portion of the location or site, or any combination thereof.

FIG. 3 illustrates a mapping 300 of one or more concentration level contours associated with an emissions detection and equipment control system at a location, according to one or more aspects of the present disclosure. A mapping 300 may comprise one or more concentration level contours, for example, concentration level contours 310, 312, and 314, associated with one or more devices 202, 204, 206, and 208 and one or more sensors 240 as discussed with respect to FIG. 2. A concentration level contour, such as any one or more concentration level contours 310, 312, and 314, depicts an area or region of a location associated with one or more concentration levels of an emission. In one or more embodiments, any one or more devices 202, 204, 206, and 208 may be within an area or region identified by or associated with a concentration level contour 310, 312, and 314 based, at least in part, on one or more types of emissions or concentration levels of one or more emissions detected and communicated by any one or more sensors 240. One or more concentration level contours 310, 312, and 314 may be generated and displayed by the control unit 118 to an operator or communicated or transmitted to one or more other information handling systems.

In one or more embodiments, a risk level may be associated with any one or more concentration level contours 310, 312, and 314. The risk level may be based on one or more industry standards, one or more environmental standards, one or more safety standards, equipment or manufacturer specifications, any other specification or standard, or any combination thereof. For example, standards and specifications may comprise any one or more of a percentage lower explosive limit, a percentage upper explosive limit, a flammability limit, a flashpoint, an Occupational Safety and Health Administration (OSHA) threshold limit, OSHA hearing protection limits, or OSHA oxygen threshold levels. In one or more embodiments, a risk level may be depicted as indicated in FIG. 3 by different types of lines. For example, the risk level of concentration level contours 310, 312, and 314 are distinguishable by the type of dashed line. In one or more embodiments, a risk level may be associated with or indicated by a color, a symbol, a pattern, an icon, an animation, or any other identifiable characteristic. In one or more embodiments, risk levels may be associated with a risk value and may range from, for example, zero to five, or any other range. For example, a risk level of zero may correspond to a low or no risk and may be represented by a color such as blue, whereas a risk level of five may correspond to a high risk and may be represented by a color such as red.

With respect to FIG. 3, a concentration level contour 310 may be indicative of an area, region, or grouping of devices 202, 204, 206, and 208 within a risk level of zero. Concentration level contour 310 may indicate that or be indicative of the type of emission or a concentration level associated with one or more emissions is above or below a threshold, within a threshold range, or meets any other condition or criteria for a risk level of zero. In one or more embodiments, a concentration level contour 312 may be associated with a risk level of one, which may correspond to a medium risk. In one or more embodiments, a concentration level contour 314 may be associated with a risk level of two, which may correspond to a high or dangerous risk. While FIG. 3 illustrates one or more concentration level contours 310, 312, 314, the present disclosure contemplates any number or quantity of concentration level contours associated with any one or more risk levels displayed or depicted in any suitable manner including but not limited to, by a numerical representation, by a shading, by a color, by a pattern, by an animation, or any other distinguishable characteristic.

A source of an emission or one or more emissions 320 may be determined based, at least in part, on data or information corresponding to or associated with one or more concentration levels of an emission detected and transmitted by one or more sensors 240. A source of an emission 320 may be a device 202, 204, 206, or 208, or may be from any other source including, but not limited to, any one or more of other site equipment, a wellbore and a surface or subsurface material at or about one or more locations. For example, in one or more embodiments, the source of an emission 320 may be determined to be an engine or a motor 202. In one or more embodiments, the source of an emission 320 may be identified as an area or region of the mapping 300. In one or more embodiments, the source of an emission 320 may be offsite (for example, at, about, or on an adjacent work site), and may appear at a boundary of the mapping 300. In one or more embodiments, the source of an emission 320 may be identified manually by the operator or automatically by an information handling system, for example, information handling system 500 of FIG. 5.

The source of an emission 320 may be identified or determined based, at least in part, on one or more concentration levels of an emission or one or more concentration level contours 310, 312, and 314. In one or more embodiments, a source of an emission 320 may be identified as or determined to be the center of a concentration level contour 310, 312, or 314 with the highest risk level. For example, a first risk level (for example, a risk level of 0) may be associated with concentration level contour 310, a second risk level (for example, a risk level of 1) may be associated with concentration level contour 312 and a third risk level (for example, a risk level of 2). In one or more embodiments, a risk level may be associated with a concentration level contour based on a predetermined threshold concentration or range of concentrations. The risk level associated with a concentration level contour may vary as the received concentration level from sensor 240 varies. For example, a risk level of 0 associated with concentration level contour 310 may change to a risk level of 1 due to an increase in a received concentration level from sensors 240 associated with one or more devices 202, 204, 206, and 208 within concentration level contour 310.

In one or more embodiments, an information handling system 500 or control unit 118 may automatically determine a source of an emission 320 based, at least in part, on one or more concentration levels outside of a predetermined threshold or predetermined range. An information handling system 500 or control unit 118 may identify the source of an emission 320 based, at least in part, on the concentration levels received from one or more sensors 240 associated with one or more devices 202, 204, 206, and 208 located in the same area or region of the location. For example, one or more devices 202, 204, 206, and 208 of a certain area or region may be associated with concentration levels that exceed the concentration levels of any one or more other devices 202, 204, 206, or 208 not in the same area or region. The information handling system 500 or control unit 118 may identify the source of an emission 320 by analyzing one or more concentration levels associated with the one or more devices 202, 204, 206, or 208 of the area or region associated with the highest concentration levels compared to other devices 202, 204, 206, or 208 of the same area or region. In one or more embodiments, the source of an emission may be identified by an operator based, at least in part, on a display of one or more concentration levels or concentration level contours, for example, any one or more concentration level contours 310, 312, and 314.

In one or more embodiments, the identification of the source of an emission 320 may trigger an automatic shutdown of one or more devices 202, 204, 206, and 208. In one or more embodiments, a source of an emission 320 may be displayed on a display, a shutdown of one or more devices 202, 204, 206 and 208 may be initiated, or both. For example, an operator may view the display and initiate a shutdown of one or more devices 202, 204, 206, and 208 based, at least in part, on the display. In one or more embodiments, a source of an emission 320 may be communicated or transmitted to an information handling system, for example, information handling system 500 in FIG. 5. In one or more embodiments, once a source of an emission 320 is determined or identified, an operation may be altered based, at least in part, on any one or more of the position, area, or region of the source of the emission 320 at the location, the type of detected emission at, about, or from the source of the emission 320, the type and quantity or number of devices 202, 204, 206, and 208 at, near, or about the source of the emission 320, or any other factors or criteria.

Figure 4:
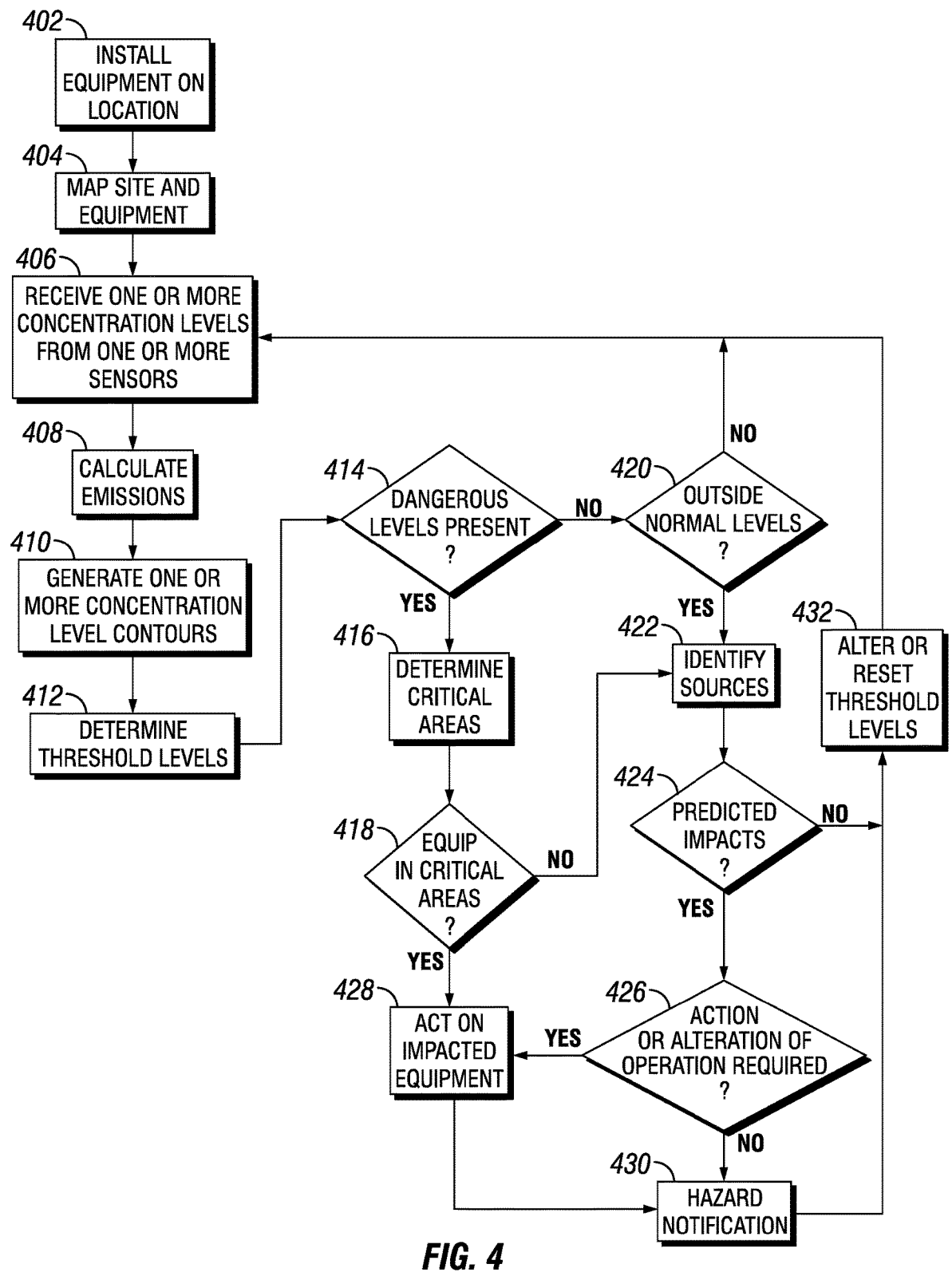
FIG. 4 is a flowchart illustrating a method of detecting emissions and controlling site equipment at a location, according to one or more aspects of the present disclosure.

FIG. 4 illustrates a flowchart illustrating a method of detecting emissions and controlling site equipment at a location, according to one or more aspects of the present disclosure. In one or more embodiments, at step 402, one or more devices 202, 204, 206, and 208 and one or more sensors 240 may be installed, positioned, or disposed at a location 200. In one or more embodiments, one or more devices 202, 204, 206, and 208 may be pre-installed or configured. At step 404, the one or more devices 202, 204, 206, and 208 and any other site equipment and the site or location may be mapped based, at least in part, on one or more user inputs or mapping technology (such as GPS technology), for example, as discussed with respect to FIG. 3. For example, a control unit 118 as discussed with respect to FIG. 1, an information handling system as discussed with respect to FIG. 5, or any other computing device disposed or positioned remotely from, at, or about the location may generate a map of the site or location, the one or more devices 202, 204, 206, and 208, any other site equipment or any combination thereof.

At step 406, a computing device, for example, control unit 118 or information handling system 500, may receive one or more concentration levels, for example, as an emissions detection signal from one or more sensors 240. The one or more concentration levels may be associated with an emission at, near, or about one or more devices 202, 204, 206, and 208. In one or more embodiments, the control unit 118 or the information handling system 500 may calculate a new concentration level in step 406 based, at least in part, on the concentration level received from sensor 240. In one or more embodiments, the new concentration level may be augmented or altered based, at least in part, on a predetermined variable, or any other factor or value. For example, the concentration level read from a sensor 240 may not reflect one or more factors or criteria associated with a concentration level of an emission, for example, a factor or criteria not measurable by sensor 240. For example, a sensor 240 may read a value of an emission such as oxygen, methane, or hydrogen sulfide which may be used to calculate a concentration level of, for example, a lower explosive limit. Alternatively, a sensor 240 may read, for example, a lower explosive limit, which may be used to calculate a concentration level of oxygen, methane, hydrogen sulfide, or any other type of emission.

At step 408, in one or more embodiments, an emission or total emission may be determined based on a mathematical model. The concentration level for an emission at a first time and a second time (or any instance of time or time interval) may be detected by a sensor 240. The rate of change of a concentration level of an emission may be determined based, at least in part, on a difference in the detected concentration level of an emission at the first time and the second time. In one or more embodiments, the rate of change in concentration level for an emission or the total emissions for a location 200 or an area or region of a location 200 may be determined based, at least in part, on the concentration level of an emission received from a sensor 240. As the map of the sensor 240 is known, the area or a volume associated with the detected concentration level may be determined. The total emissions for a location may be determined based, at least in part, on the determined rate of change of one or more concentration levels of one or more emissions.

At step 410, one or more concentration level contours (for example, concentration level contours 310, 312, and 314 as illustrated in FIG. 3) are generated. The concentration level contours may be generated based, at least in part, on one or more concentration levels of an emission received from one or more sensors 240 at step 406. A concentration level contour may represent or be associated with a concentration level of one or more devices or an area or region comprising one or more devices, for example, devices 202, 204, 206, and 208 of FIG. 2. In one or more embodiments, the generated concentration level contours may be displayed at a computing device, for example, on a display of control unit 118 or information handling system 500.

At step 412, a control unit 118 or information handling system 500 may determine one or more threshold concentration levels. The threshold concentration level may be an input received from a user, a measured value, or value based on any combination thereof. For example, in one or more embodiments, the control unit 118 or information handling system 500 may receive or retrieve a predetermined value as the threshold concentration level from a user or stored location. In one or more embodiments, the control unit 118 or information handling system 500 may determine a threshold concentration level based, at least in part, on a concentration level initially received from the one or more sensors 240 at step 406. In one or more embodiments, the threshold concentration level may be equal to the concentration level received in step 406. In one or more embodiments, the threshold concentration level may be based on a received concentration level of emissions in combination with one or more factors received from a user or an operator. Once the control unit 118 or information handling system 500 determines a threshold concentration level, the threshold concentration level may remain static or may be recalculated each time a concentration level is received from a sensor 240.

At step 414, the control unit 118 or information handling system 500 may determine whether dangerous concentration levels are present based, at least in part, on a comparison of the received concentration level from the one or more sensors 240 to the threshold concentration level. In one or more embodiments, the control unit 118 or information handling system 500 may determine a dangerous concentration level is present when the received concentration level from the one or more sensors 240 exceeds or is equal to the threshold concentration level.

In one or more embodiments, if a dangerous concentration level is present, then at step 416, the control unit 118 or information handling system 500 may determine one or more critical areas. In one or more embodiments, the control unit 118 or information handling system 500 may determine a dangerous concentration level is not present when the received concentration level from the one or more sensors 240 does not exceed or is equal to the threshold concentration level. If a dangerous level is not present, then the control unit 118 or information handling system 500 may determine whether the concentration level is outside normal levels in step 420. In one or more embodiments, an alteration of an operation or mode may be triggered when a dangerous concentration level is present. In one or more embodiments, an alteration may comprise one or more of an automatic alarm and a shutdown, ramp-down, or other alteration of operation on one or more devices 202, 204, 206, and 208. The type of alteration may be predetermined or may vary based on the type of device 202, 204, 206, or 208 that triggered the alteration. In one or more embodiments, for example, a shutdown may be appropriate where the device, such as an engine, may experience run-away or cause further damage to the equipment. In one or more embodiments, a condition of the concentration level exceeding the threshold concentration level may not have immediate impacts, and therefore may only generate a warning or notification. An impact may comprise, for example, any condition associated with a device or an environment surrounding the device. An operator may initiate an alarm, shutdown, ramp-down, or other alteration of operation of the device 202, 204, 206, or 208 based, at least in part, on the warning or notification.

At step 416, the control unit 118 or information handling system 500 may determine one or more critical areas or impacted regions before triggering an alteration of an operation on any one or more devices 202, 204, 206, or 208. Critical areas may be determined by areas or regions where the concentration levels exceed a threshold concentration level (for example, predetermined concentration level based on one or more user inputs or determined by the control unit 118 or information handling system 500). For example, the control unit 118 or information handling system 500 may survey any one or more of the devices 202, 204, 206, or 208 associated with the concentration level of an emission received from the sensor 240 to determine if a detected concentration level of emission may cause one or more impacts (such as a negative impact) on any one or more of the devices 202, 204, 206 or 208. A negative impact may comprise overspeed or run-away of an engine, unexpected shutdown of a generator, damage to any one or more devices 202, 204, 206, or 208, potential harm to personnel in the area, or any other adverse impact on or at a location, device, personnel, or any other resource.

At step 418, the control unit 118 or information handling system 500 may determine whether a device is an impacted device, for example, that a device is associated with a critical area or region identified in step 416 as an impacted region. In one or more embodiments, an impacted device may be a device associated with an impacted region. An impacted device may comprise one or more devices 202, 204, 206, or 208 that are associated with the impacted region. In one or more embodiments, the control unit 118 or information handling system 500 may determine that, despite the received concentration level of an emission exceeding the threshold concentration level, no action is required. The critical areas or impacted regions may not comprise any devices that would be damaged or negatively impacted by the detected concentration level of emissions, or may not contain any devices that would interact with the detected emission. For example, an engine 202 may experience run-away or overspeed when exposed to certain emissions, whereas a tank 204 would operate normally when exposed to the same emissions. In one or more embodiments, a critical area or impacted region may be an area of the location where a concentration level of an emission exceeds a threshold value. For example, a region where a concentration level of an emission exceeds 85% of a lower explosive limit may be determined or defined to be a critical area. A threshold value used to determine one or more critical areas may be based on one or more industry standards, one or more environmental standards, one or more safety standards, equipment or manufacturer specifications, any other specification or standard, or any combination thereof. For example, standards and specifications that a critical area may be based on may include a percentage lower explosive limit, a percentage upper explosive limit, a flammability limit, a flashpoint, an Occupational Safety and Health Administration (OSHA) threshold limit, OSHA hearing protection limits, or OSHA oxygen threshold levels. If the control unit 118 or information handling system 500 determines that no devices 202, 204, 206, or 208 are in at least one of the one or more critical areas, then in step 422, the control unit 118 or information handling system 500 may identify one or more sources of an emission 320. If the control unit 118 or information handling system 500 identifies one or more devices 202, 204, 206, or 208 in one or more critical areas, the control unit 118 or information handling system 500 may initiate action or alteration on the one or more devices 202, 204, 206, or 208 in step 428.

In one or more embodiments, operation of one or more devices 202, 204, 206, and 208 may be altered even when the concentration level received from one or more sensors 240 does not meet or exceed the threshold concentration level. For example, a display or other information (such as a graph illustrating historical concentration levels) may be used to predict that within a certain period of time a concentration level will meet or exceed a threshold concentration level. An operation of one or more devices 202, 204, 206, and 208 may then be preemptively altered based on the prediction. Such predictions are discussed as well with respect to step 424.

At step 420, the control unit 118 or information handling system 500 may determine whether or not the received concentration level is outside normal levels, despite not exceeding the threshold concentration level. "Normal levels" may be defined based, at least in part, on past received concentration levels or concentration levels inputted by a user. A condition outside of normal levels may include, for example, a spike in emission levels over a short period of time, although it may not exceed the threshold concentration level. In one or more embodiments, the control unit 118 or information handling system 500 may use a trend of received concentration levels (for example, a graph or other display of historical data of concentration levels) or a single received concentration level to determine if the concentration level is outside of normal levels. In one or more embodiments, the control unit 118 or information handling system 500 may determine that the concentration level received by sensor 240 may cause harmful effects on the equipment or personnel in the identified critical area and may initiate a shutdown or some other action. Conversely, the control unit 118 or information handling system 500 may determine the condition does not require action. If the control unit 118 or information handling system 500 determines the received concentration level is outside of normal levels, then at step 422, the control unit 118 or information handling system 500 may identify one or more sources of an emission 320 associated with the one or more concentration levels as discussed with respect to step 422. If the control unit 118 or information handling system 500 determines the received concentration level is not outside normal levels, the control unit 118 or information handling system may return to step 406.

At step 422, in one or more embodiments, the control unit 118 or information handling system 500 may automatically identify one or more sources of an emission 320. The source of an emission 320 may be identified based, at least in part, on the received concentration levels from sensors 240 or the concentration level contours generated from the received concentration levels. In one or more embodiments, for example, the control unit 118 or information handling system 500 may determine the source of an emission 320 to be a device 202, 204, 206, or 208 where the highest concentration levels converge. In one or more embodiments, the source of an emission 320 may not be an identifiable device 202, 204, 206, or 208, and may be any object or location at the work site. In one or more embodiments, the source of an emission 320 may be an object, device, or any other source remote from the work site, for example, a device positioned or disposed at or about an adjacent or nearby work site and may be at or about the surface or below the surface such as subsea or subterranean.

The control unit 118 or information handling system 500 may predict potential impacts as shown in step 424. A predicted impact may comprise a determination that detected levels will soon exceed a threshold concentration level (for example, a level that has been determined to be a dangerous level) near operating equipment, for example, one or more devices 202, 204, 206, or 208. Predicted impacts may be based on received concentration levels and risk levels associated with the concentration level contours. For example, in FIG. 3, concentration level contour 314 with a high risk level may have negative impacts (predicted or unpredicted) such as damage or harm to the one or more devices 202, 204, 206, or 208. As another example, a higher risk level could have more severe negative impacts such as damage or harm to downstream devices 202, 204, 206, or 208 in addition to the devices 202, 204, 206, or 208 within the concentration level contour 314 than a lower risk level. In one or more embodiments, one or more predicted impacts may comprise a required shutdown of one or more devices 202, 204, 206, or 208. The ability to predict impacts by control unit 118 or information handling system 500 may prevent unnecessary shutdown of one or more devices 202, 204, 206, or 208, or minimize the damage or harm to one or more devices 202, 204, 206, or 208. For example, a shutdown of a generator 202 may result in a shutdown of one or more devices 202, 204, 206, or 208 powered by or coupled to the generator 202. Prediction of a shutdown may allow time for an operator or control unit 118 or information handling system 500 to couple the one or more devices 202, 204, 206, or 208 to another generator, a generator 204 for example, before shutdown of the generator 202. The ability to predict impacts may reduce the effect of such impacts on the operation of equipment, for example, one or more devices 202, 204, 206, or 208, at a work site. In one or more embodiments, an impact may be a predicted impact. A predicted impact may be based on one or more alterations or changes that occur at a device or equipment or to one or more environmental resources. In one or more embodiments, a predicted impact may be associated with a determination or a prediction that a concentration level of an emission will exceed a predetermined threshold within or at a determined time. For example, a predicted impact may indicate that at the determined time a device will be shut down due to the prediction that a concentration level of an emission will exceed a predetermined threshold. In one or more embodiments, one or more actions or operations may be altered to minimize one or more effects associated with a predicted impact. For example, any one or more of a controlled shutdown may be initiated on a device associated with the predicted impact to prevent damage to the device or the surrounding environment, a load of a device associated with the predicted impact may be transferred or altered, an operation may be performed or scheduled to alter the concentration level of the emission, or any one or more actions or preventative steps may be initiated or performed.

If the control unit 118 or information handling system 500 does not identify or determine any predicted impacts, the control unit 118 or information handling system 500 may proceed to step 432. If one or more predicted impacts have been identified or determined, then at step 426, the control unit 118 or information handling system 500 may determine whether or not a predicted impact necessitates an action or an alteration of an operation based, at least in part, on the risk level of the predicted impact.

If the control unit 118 or information handling system 500 determines an action or alteration is required, then an action on or alteration of one or more devices 202, 204, 206, or 208 may be initiated at step 428. For example, the control unit 118 or information handling system 500 may transmit a signal to shut down or ramp down one or more devices, for example, one or more devices 202, 204, 206, or 208 of FIG. 2. The type of action or alteration may be predetermined or may vary based on the type of device 202, 204, 206, or 208 that triggered the action or alteration. In one or more embodiments, for example, a shutdown may be appropriate where a device, such as an engine, may experience run-away or cause damage to the engine, other devices, or operators. In one or more embodiments, one or more devices 202, 204, 206, or 208 may be unaffected by the predicted impact, and therefore, an alteration or other action may be unnecessary. If the control unit 118 or information handling system 500 determines no alteration or action on a device 202, 204, 206, or 208 is required, the control unit 118 or information handling system 500 may proceed to step 430.

At step 430, a notification comprising information associated with the predicted impact, the concentration level of the emission, or both may be transmitted, displayed, or otherwise communicated to an operator or other personnel based on the signal. In one or more embodiments, for example, a notification may be an audible alarm, light, or other visible display. In one or more embodiments, the notification may be displayed or communicated after an action is performed or initiated in step 428 at or on one or more devices 202, 204, 206, or 208. In one or more embodiments, the notification may be displayed despite no action or alteration being performed or initiated on any one or more devices 202, 204, 206, or 208. In one or more embodiments, an operator may initiate an alarm, shutdown, ramp-down, or other alteration of operation of one or more devices 202, 204, 206, or 208 based, at least in part, on a warning or notification.

At step 432, the threshold concentration level may be changed, altered, or reset based, at least in part, on a previous predetermined threshold concentration level or a received threshold concentration level. In one or more embodiments, the threshold concentration level may be determined based, at least in part, on a previously received concentration level from one or more sensors 240. For example, a sensor 240 may transmit a baseline concentration level prior to any site equipment, for example, devices 202, 204, 206 and 208 being power-up or utilized for use as an initial threshold concentration level. If no baseline concentration level is transmitted, the threshold concentration level may be initially set to zero. In one or more embodiments, a threshold concentration level may be used to determine a change in a concentration level based on subsequently received concentration levels. A threshold concentration level may be based, at least in part, on a baseline concentration level or the baseline concentration level and any one or more other factors or criteria, including but not limited to, any one or more sources. In one or more embodiments, a threshold concentration level may be altered, augmented, replaced, or otherwise changed from a previously received or determined threshold concentration level associated with one or more sources based, at least in part, on one or more of a user input, a standard, an entry in a database, a condition or criteria, and a previously received threshold concentration level. For example, a first threshold concentration level may be replaced by a second threshold concentration level. The threshold concentration level may be changed, altered, or controlled manually by a user or automatically by the control unit 118 or information handling system 500. For example, an operator may manually alter a valve, instrument, or a setting of a device 202, 204, 206, or 208 or an associated sensor 240 that causes a threshold concentration level to be set or changed, or a threshold concentration level may be set or changed through an interface of the control unit 118 or information handling system 500. In one or more embodiments, the control unit 118 or information handling system 500 may automatically change or alter the threshold concentration level based, at least in part, on any one or more concentration levels associated with a source of an emission 320.

Figure 5:
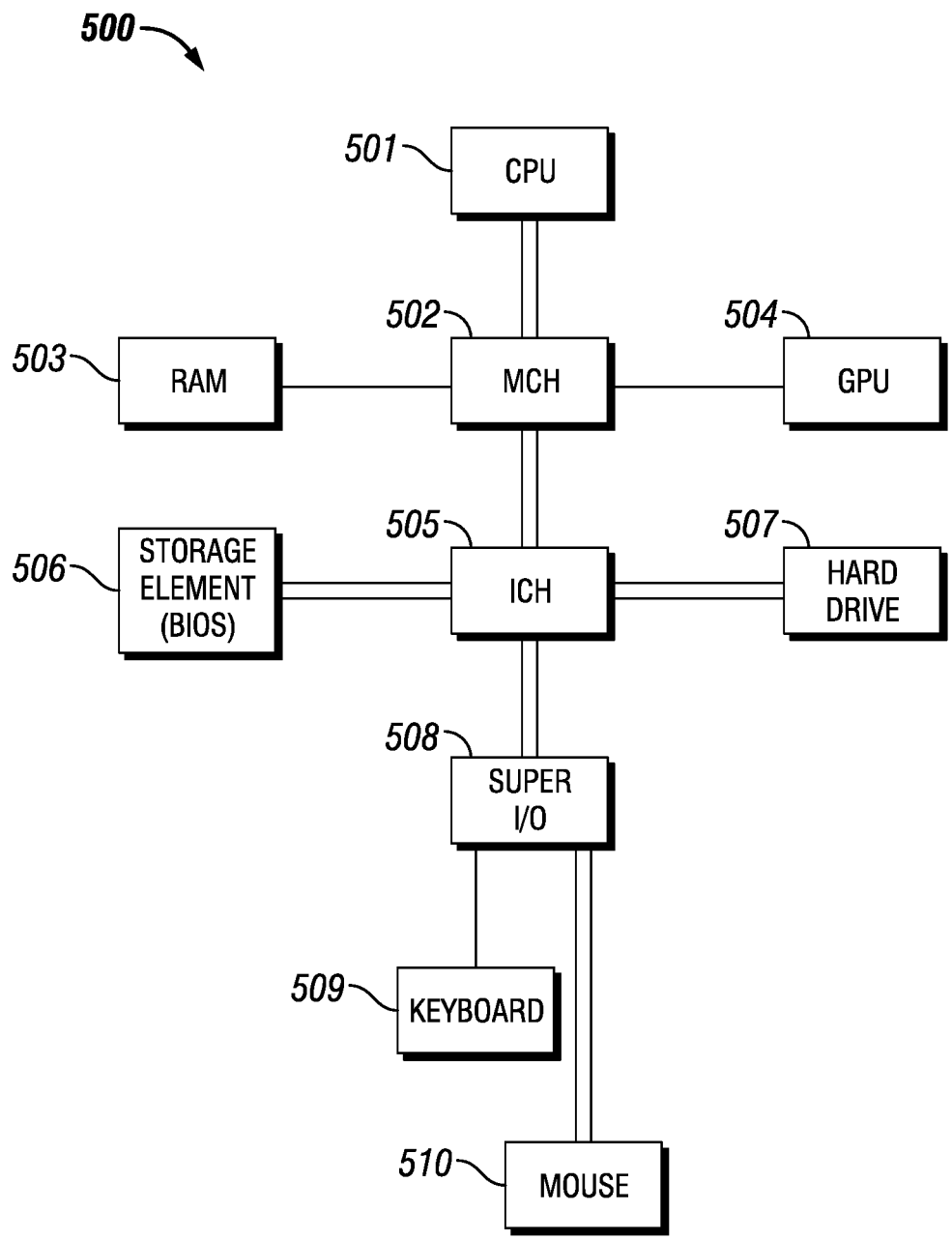
FIG. 5 is a diagram illustrating an information handling system, according to one or more aspects of the present disclosure.

FIG. 5 is a diagram illustrating an example information handling system, according to aspects of the present disclosure. The control unit 118 may take a form similar to the information handling system 500. A processor or central processing unit (CPU) 501 of the information handling system 500 is communicatively coupled to a memory controller hub (MCH) or north bridge 502. The processor 501 may include, for example a microprocessor, microcontroller, digital signal processor (DSP), application specific integrated circuit (ASIC), or any other digital or analog circuitry configured to interpret and/or execute program instructions and/or process data. Processor 501 may be configured to interpret and/or execute program instructions or other data retrieved and stored in any memory such as memory 503 or hard drive 507. Program instructions or other data may constitute portions of a software or application for carrying out one or more methods described herein. Memory 503 may include read-only memory (ROM), random access memory (RAM), solid state memory, or disk-based memory. Each memory module may include any system, device or apparatus configured to retain program instructions and/or data for a period of time (for example, computer-readable non-transitory media). For example, instructions from a software program or application may be retrieved and stored in memory 503 for execution by processor 501.

Modifications, additions, or omissions may be made to FIG. 5 without departing from the scope of the present disclosure. For example, FIG. 5 shows a particular configuration of components of information handling system 500. However, any suitable configurations of components may be used. For example, components of information handling system 500 may be implemented either as physical or logical components. Furthermore, in one or more embodiments, functionality associated with components of information handling system 500 may be implemented in special purpose circuits or components. In one or more embodiments, functionality associated with components of information handling system 500 may be implemented in configurable general purpose circuit or components. For example, components of information handling system 500 may be implemented by configured computer program instructions.

Memory controller hub 502 may include a memory controller for directing information to or from various system memory components within the information handling system 500, such as memory 503, storage element 506, and hard drive 507. The memory controller hub 502 may be coupled to memory 503 and a graphics processing unit (GPU) 504. Memory controller hub 502 may also be coupled to an I/O controller hub (ICH) or south bridge 505. I/O controller hub 505 is coupled to storage elements of the information handling system 500, including a storage element 506, which may comprise a flash ROM that includes a basic input/output system (BIOS) of the computer system. I/O controller hub 505 is also coupled to the hard drive 507 of the information handling system 500. I/O controller hub 505 may also be coupled to a Super I/O chip 508, which is itself coupled to several of the I/O ports of the computer system, including keyboard 509 and mouse 510.

In one or more embodiments, a method for detecting a concentration of an emission comprises mapping one or more devices at a location, wherein one or more sensors are positioned on the one or more devices, and wherein the location comprises one or more regions, receiving one or more concentration level measurements associated with one or more emissions from at least one of the one or more sensors; determining one or more concentration levels based, at least in part, on the one or more concentration level measurements; determining one or more impacted regions of the one or more regions based, at least in part, on a comparison of the one or more concentration levels to one or more threshold concentration levels; identifying one or more impacted devices associated with the one or more impacted regions, wherein the one or more impacted devices comprise at least one of the one or more devices; and altering an operation of at least one of the one or more devices based, at least in part, on one or more impacts associated with the one or more impacted regions. In one or more embodiments, the method for detecting a concentration of an emission comprises mapping one or more devices at a location based, at least in part, on global position system (GPS) data. In one or more embodiments, the method for detecting a concentration of an emission comprises generating a concentration level contour map based, at least in part, on the one or more concentration levels. In one or more embodiments, the method for detecting a concentration of an emission comprises indicating the one or more concentration levels on a concentration level contour map. In one or more embodiments, the method for detecting a concentration of an emission comprises generating an alarm based, at least in part, on the comparison of the one or more concentration levels to the one or more threshold concentration levels. In one or more embodiments, the method for detecting a concentration of an emission comprises initiating a shutdown of the at least one of the one or more devices.

In one or more embodiments, an emissions concentration detection system comprises one or more sensors associated with one or more devices at a location, wherein at least one of the one or more sensors detect a concentration of one or more emissions for a region of the location, wherein the region comprises at least one of the one or more devices; and an information handling system communicatively coupled to the one or more sensors, the information handling system comprising: a processor and a non-transitory memory coupled to the processor, wherein the non-transitory memory comprises one or more instructions that, when executed by the processor, cause the processor to: map one or more devices at a location, wherein one or more sensors are positioned on the one or more devices; receive one or more concentration level measurements associated with one or more emissions from at least one of the one or more sensors; determine one or more concentration levels based, at least in part, on the one or more concentration level measurements; determine one or more impacted regions of the one or more regions based, at least in part, on a comparison of the one or more concentration levels to one or more threshold concentration levels; identify one or more impacted devices associated with the one or more impacted regions, wherein the one or more impacted devices comprise at least one of the one or more devices; and alter an operation of at least one of the one or more devices based, at least in part, on the one or more impacts associated with the one or more impacted regions. In one or more embodiments, the emissions concentration detection system, wherein the one or more instructions that, when executed by the processor, further cause the processor to map one or more devices at a location based, at least in part, on global positioning system (GPS) data. In one or more embodiments, the emissions concentration detection system, wherein the one or more instructions that, when executed by the processor, further cause the processor to generate a concentration level contour map based, at least in part, on the one or more concentration levels. In one or more embodiments, the emissions concentration detection system, wherein the one or more instructions that, when executed by the processor, further cause the processor to indicate the one or more concentration levels on a concentration level contour map. In one or more embodiments, the emissions concentration detection system, wherein the one or more instructions that, when executed by the processor, further cause the processor to generate an alarm based, at least in part, on the comparison of the one or more concentration levels to the one or more threshold concentration levels. In one or more embodiments, the emissions concentration detection system further comprises one or more instructions that, when executed by the processor, further cause the processor to identify a source of at least one of the one or more emissions, wherein the source comprises at least one of the one or more impacted devices. In one or more embodiments, the emissions concentration detection system, wherein the one or more instructions that, when executed by the processor, further cause the processor to alter the operation of the at least one of the one or more devices, wherein altering the operation further comprises initiating a shutdown of the at least one of the one or more devices.

In one or more embodiments, a non-transitory storage computer readable medium storing one or more instructions that, when executed, may cause a processor to: map one or more devices at a location, wherein one or more sensors are positioned on the one or more devices, and wherein the location comprises one or more regions; receive one or more concentration level measurements associated with one or more emissions from at least one or more sensors; determine one or more concentration levels based, at least in part, on the one or more concentration level measurements; determine one or more impacted regions of the one or more regions based, at least in part, on a comparison of the one or more concentration levels to one or more threshold concentration levels; identify one or more impacted devices associated with the one or more impacted regions, wherein the one or more impacted devices comprise at least one of the one or more devices; and alter an operation of at least one of the one or more devices based, at least in part, on the one or more impacts associated with the one or more impacted regions. In one or more embodiments, the non-transitory storage computer readable medium, wherein the one or more instructions, that when executed by the processor, further cause the processor to generate a concentration level contour map based, at least in part, on the one or more concentration levels. In or more embodiments, the non-transitory storage computer readable medium, wherein the one or more instructions, that when executed by the processor, further cause the processor to indicate the one or more concentration levels on a concentration level contour map. In one or more embodiments, the non-transitory storage computer readable medium, wherein the one or more instructions, that when executed by the processor, further cause the processor to generate an alarm based, at least in part, on the comparison of the one or more concentration levels to the one or more threshold concentration levels. The non-transitory storage computer readable medium, wherein the one or more instructions, that when executed by the processor, further cause the processor to identify a source of at least one of the one or more emissions, wherein the source comprises at least one of the one or more impacted devices. The non-transitory storage computer readable medium, wherein the one or more instructions, that when executed by the processor, further cause the processor to alter the operation of the at least one of the one or more devices, wherein altering the operation further comprises initiating a shutdown of the at least one of the one or more devices.

What is claimed is:

1. A method for detecting a concentration of an emission, comprising:
mapping one or more devices at a location, wherein one or more sensors are positioned on the one or more devices, and wherein the location comprises one or more regions;
receiving one or more concentration level measurements associated with at least two types of emissions from at least one of the one or more sensors, wherein the at least two types of emissions includes two or more of a gas, a fluid, a vapor, a noise, a light or a particulate matter;

determining one or more concentration levels based, at least in part, on the one or more concentration level measurements;
determining one or more impacted regions of the one or more regions based, at least in part, on a comparison of the one or more concentration levels to one or more threshold concentration levels;
identifying one or more impacted devices associated with the one or more impacted regions, wherein the one or more impacted devices comprise at least one of the one or more devices; and
altering an operation of at least one of the one or more impacted devices based, at least in part, on one or more impacts associated with the one or more impacted regions.

2. The method of claim 1, wherein one or more devices at the location are mapped based, at least in part, on global positioning system (GPS) data.

3. The method of claim 1, further comprising generating a concentration level contour map based, at least in part, on the one or more concentration levels.

4. The method of claim 1, further comprising indicating the one or more concentration levels on a concentration level contour map.

5. The method of claim 1, further comprising generating an alarm based, at least in part, on the comparison of the one or more concentration levels to the one or more threshold concentration levels.

6. The method of claim 1, further comprising identifying a source of at least one of the at least two types of emissions, wherein the source comprises at least one of the one or more impacted devices.

7. The method of claim 1, wherein altering the operation of the at least one of the one or more devices comprises initiating a shutdown of the at least one of the one or more devices.

8. An emission concentration detection system, comprising:
one or more sensors associated with one or more devices at a location, wherein at least one of the one or more sensors detect a concentration of at least two types emissions for one or more regions of the location, wherein the region comprises at least one of the one or more devices, wherein the at least two types of emissions includes two or more of a gas, a fluid, a vapor, a noise, a light or a particulate matter; and
an information handling system communicatively coupled to the one or more sensors, the information handling system comprising:
a processor; and
a non-transitory memory coupled to the processor, wherein the non-transitory memory comprises one or more instructions that, when executed by the processor, cause the processor to:
map the one or more devices at a location, wherein one or more sensors are positioned on the one or more devices;
receive one or more concentration level measurements associated with the at least two types of emissions from the at least one of the one or more sensors;
determine one or more concentration levels based, at least in part, on the one or more concentration level measurements;
determine one or more impacted regions of the one or more regions based, at least in part, on a comparison of the one or more concentration levels to one or more threshold concentration levels;
identify one or more impacted devices associated with the one or more impacted regions, wherein the one or more impacted devices comprise at least one of the one or more devices; and
alter an operation of at least one of the one or more impacted devices based, at least in part, on one or more impacts associated with the one or more impacted regions.

9. The system of claim 8, wherein the one or more instructions that, when executed by the processor, further cause the processor to map one or more devices at a location based, at least in part, on global positioning system (GPS) data.

10. The system of claim 8, wherein the one or more instructions that, when executed by the processor, further cause the processor to generate a concentration level contour map based, at least in part, on the one or more concentration levels.

11. The system of claim 8, wherein the one or more instructions that, when executed by the processor, further cause the processor to indicate the one or more concentration levels on a concentration level contour map.

12. The system of claim 8, wherein the one or more instructions that, when executed by the processor, further cause the processor to generate an alarm based, at least in part, on the comparison of the one or more concentration levels to the one or more threshold concentration levels.

13. The system of claim 8, wherein the one or more instructions that, when executed by the processor, further cause the processor to identify a source of at least one of the at least two types of emissions, wherein the source comprises at least one of the one or more impacted devices.

14. The system of claim 8, wherein the one or more instructions that, when executed by the processor, further cause the processor to alter the operation of the at least one of the one or more devices, wherein altering the operation further comprises initiating a shutdown of the at least one of the one or more devices.

15. A non-transitory storage computer readable medium storing one or more instructions that, when executed, cause a processor to:
map one or more devices at a location, wherein one or more sensors are positioned on the one or more devices, and wherein the location comprises one or more regions;
receive one or more concentration level measurements associated with at least two types of emissions from at least one of the one or more sensors, wherein the at least two types of emissions may include two or more of a gas, a fluid, a vapor, a noise, a light or a particulate matter;
determine one or more concentration levels based, at least in part, on the one or more concentration level measurements;
determine one or more impacted regions of the one or more regions based, at least in part, on a comparison of the one or more concentration levels to one or more threshold concentration levels;
identify one or more impacted devices associated with the one or more impacted regions, wherein the one or more impacted devices comprise at least one of the one or more devices; and
alter an operation of at least one of the one or more impacted devices based, at least in part, on the one or more impacts associated with the one or more impacted regions.

16. The non-transitory storage computer readable medium of claim 15, wherein the one or more instructions, that when executed by the processor, further cause the processor to generate a concentration level contour map based, at least in part, on the one or more concentration levels.

17. The non-transitory storage computer readable medium of claim 15, wherein the one or more instructions, that when executed by the processor, further cause the processor to indicate the one or more concentration levels on a concentration level contour map.

18. The non-transitory storage computer readable medium of claim 15, wherein the one or more instructions, that when executed by the processor, further cause the processor to generate an alarm based, at least in part, on the comparison of the one or more concentration levels to the one or more threshold concentration levels.

19. The non-transitory storage computer readable medium of claim 15, wherein the one or more instructions, that when executed by the processor, further cause the processor to identify a source of at least one of the at least two types of emissions, wherein the source comprises at least one of the one or more impacted devices.

20. The non-transitory storage computer readable medium of claim 15, wherein the one or more instructions, that when executed by the processor, further cause the processor to alter the operation of the at least one of the one or more devices, wherein altering the operation further comprises initiating a shutdown of the at least one of the one or more devices.

* * * * *